United States Patent
Umeki et al.

(10) Patent No.: US 7,476,834 B2
(45) Date of Patent: Jan. 13, 2009

(54) DIAGNOSIS SYSTEM INCLUDING CORRELATING RADIOGRAPHED IMAGE DATA WITH PATIENT INFORMATION

(75) Inventors: Mamoru Umeki, Hachioji (JP); Jiro Okuzawa, Hachioji (JP); Wataru Motoki, Hachioji (JP)

(73) Assignee: Konica Minolta Medical & Graphic Inc., Tokyo (JP)

( * ) Notice: Subject to any disclaimer, the term of this patent is extended or adjusted under 35 U.S.C. 154(b) by 0 days.

(21) Appl. No.: 11/731,205

(22) Filed: Mar. 29, 2007

(65) Prior Publication Data

US 2007/0269017 A1    Nov. 22, 2007

(30) Foreign Application Priority Data

Apr. 5, 2006    (JP)    .............................. 2006-104363

(51) Int. Cl.
*H01L 27/00*    (2006.01)
(52) U.S. Cl. .............................. 250/208.1; 250/559.46
(58) Field of Classification Search .............. 250/208.1, 250/559.4, 559.46, 363.04, 370.09; 378/62, 378/165, 8, 95, 98.2, 98.5, 114–117; 382/128–132, 382/274; 600/443, 101, 429, 407
See application file for complete search history.

(56) References Cited

U.S. PATENT DOCUMENTS

| | | | |
|---|---|---|---|
| 5,334,851 A | 8/1994 | Good | |
| 7,197,529 B2 * | 3/2007 | Nakagawa et al. | .......... 709/200 |
| 2005/0222871 A1 | 10/2005 | Motoki | |

FOREIGN PATENT DOCUMENTS

| | | | |
|---|---|---|---|
| JP | 2002-159476 A | 6/2002 |
| JP | 2002-311524 A | 10/2002 |
| JP | 2006-25830 A | 2/2006 |

OTHER PUBLICATIONS

International Search Report dated Apr. 17, 2007 issued in counterpart International Application No. PCT/JP2007/056174.

* cited by examiner

*Primary Examiner*—Que T Le
(74) *Attorney, Agent, or Firm*—Frishauf, Holtz, Goodman & Chick, P.C.

(57) ABSTRACT

A diagnosis system includes an image generating apparatus for forming photographed image data and a control apparatus, wherein the image generating apparatus includes an FPD having an image generating device for forming the photographed data, an image memory capable of storing the photographed image data formed by the image generating device in order of photographing and a communication section 236 capable of transmitting the photographed image data stored in the image memory to the control apparatus, and the control apparatus includes a communication section 36 for receiving the photographed image data transmitted from the communication section 236 and a CPU for correlating the photographed image data received by the communication section 36 with patient information of the patient corresponding to the photographed image data.

4 Claims, 8 Drawing Sheets

| RECEPTION DATE | RECEPTION NO. | PATIENT INFORMATION | NUMBER OF IMAGES | NUMBER OF CONTRAST AGENT IMAGES | MODALITY | REGION | MEDICATION | NAME OF INJURY OR DISEASE | COMMENT | INSURANCE POINT | |
|---|---|---|---|---|---|---|---|---|---|---|---|
| 2006/1/12 | 1 | SATO ICHIRO | 0 | 0 | - | - | MEDICINE A 5mm 1 TABLET<br>MEDICINE B 2.5mm 1 TABLET<br>... | aaa | | 400 | ... |
| 2006/1/12 | 2 | SUZUKI JIRO | 2 | 1 | CR | CHEST | - | bbb | ... | 548 | ... |
| ... | ... | ... | ... | ... | ... | ... | ... | ... | ... | ... | ... |

FIG. 8

DIAGNOSIS SYSTEM INCLUDING CORRELATING RADIOGRAPHED IMAGE DATA WITH PATIENT INFORMATION

This application is based on Japanese Patent Application No. 2006-104363 filed on Apr. 5, 2006 in Japanese Patent Office, the entire content of which is hereby incorporated by reference.

BACKGROUND OF THE INVENTION

The present invention relates to a diagnosis system, which is mainly used at small-scale medical facilities.

There has been known a diagnosis system, in which a technician uses an image generating apparatus, such as a CR (Computed Radiography) apparatus and the same to photograph a subject patient, who has visited a medical facility, applies an image processing, such as a gradation processing, onto the obtained images and operates to output the images, to which the image processing has been applied, so that a medical doctor can analyze the medical images.

With respect to the diagnosis system, a plurality of persons in charge play respective roles to proceed the diagnosis as following. A receptionist receives a patient, who has visited the medical facility, and issues an examination order (a receptionist); A technician actually radiographs the patient in the radiographing room and forms digital image data; A technician (who has been selected from general technicians) or the same determines whether or not the gradation of the image is capable of being used for diagnosis and corrects the contrast and density of the image if necessary; And a person in charge of analyzing (a medical doctor) determines whether or not there is an illness based on the image.

In large scale medical facilities (they will be called large scale facilities hereinafter) in which conventional diagnosis systems are supposed to be used, there exist a plurality of image generating apparatuses and a plurality of technicians for operating the image generating apparatuses, and there are separately provided a console for operating the image generating apparatus for the plurality of technicians and a viewer by which the medical doctor checks the image data, as sharing respective roles. Thus, there has been a possibility that the patient mismatches with his or her image data by mistake. Accordingly, in order to prevent this, a system for connecting respective apparatuses through network, issuing ID at respective apparatuses and correlating the results of work processes of the respective apparatuses with each other is proposed (for example, see Patent Document 1).

With respect to the location for playing the roles described above in these systems, in many hospitals, a reception desk and a radiology department are separately and remotely located. For example, the reception desk is located in the first floor and the radiology department is located in the basement. Further, it is common that a plurality of technicians use a plurality of radiographing apparatuses to simultaneously execute radiographing and a plurality of patients constantly exist at respective processes. In order to prevent the mistake occurring in the correlation of the formed image with the patient, methods for adding ID onto works of respective process and correlating respective works with each other via a network of HIS (Hospital Information System) and RIS (Radiology Information System) are conducted (for example, see Patent Documents 2 and 3).

For example, at the reception desk located in the first floor, examination items (radiographic items) are determined based on interview of a patient and the examination items are registered together with the patient name. Based on this action, a patient list, to which additional patient information will be added whenever it is necessary, is generated and the patient list will be displayed on the workstation (it will be called "WS" hereinafter), which is set on the reception desk located in the first floor. Simultaneously, the patient list described above is displayed on the console located in the radiography department located in B1 (basement) via network of RIS/HIS. (Here, a "console" denotes a workstation for displaying the settings of radiography condition, examination order information of RIS/HIS and images obtained by radiographing the patient. It is common that the total number of the consoles is plural in order to improve the decentrized processing efficiency. These consoles are connected each other via network. When a predetermined ID has been selected at a console out of the consoles, in order to avoid duplicated radiographing in the plurality of technicians, a method for making the patient list to notify that the examination is under process is utilized (for example, flashing display, changing the color of the patient list or outputting beep sound when the same inspection is specified).

The technician of the radiography department selects the examination ID to be radiographed from now on in the displayed patient lists by using the console located near the technician, and registers the ID (the cassette ID) of a CR plate (cassette) to be used. Based on this action, for example, the registered cassette ID is displayed in the cassette ID column of the patient list. The technician, for example, brings three cassettes with him or her and moves to a radiographing room to take radiation images of the patient. After that the cassette, onto which radiation images have been recorded, is read by a reading apparatus. The reading apparatus reads the cassette ID adhered onto the cassette, which has been inserted therein, transmits the cassette ID together with image data and finally correlates the examination ID (a patient ID) with the generated image data. The generated image data is transmitted to the console, by which the technician had selected the examination ID, and is displayed on the console. At this step, the technician checks the radiation image positioning, conducts radiographing again when the positioning is not appropriate, and determines whether or not the density and contrast corrections and a frequency emphasis process should be applied. After that the generated image data is stored in an analysis-waiting (diagnosis-waiting) server. A medical doctor for analyzing images analyzes the image (conducts diagnosis) by selecting and displaying the image related to a predetermined patient out of images, which have been stored in the analysis-waiting server on the workstation in a diagnosis room (many of the workstations have a high definition monitor for the viewer function).

In the system utilized in a large scale facility described above, with respect to the information affecting medical insurance point calculation, such as whether or not the radiographing conducted for the patient is simple radiographing or radiographing using a contrast agent (medium), the system is arranged to be able to consolidate the all information items into RIS /HIS sever for controlling by registering the examination ID of the patient, the cassette ID, and correlating the photographed images to the patient.

However, according to the survey conducted by the inventors of this invention, in the case of relatively small scale medical facilities (it will be called small scale facilities hereinafter) such as a small medical clinic, in many cases, the image generating apparatuses installed are not many. Further, in many cases, an assistant to the medical doctor conducts positioning of the patient when radiographing, and the medical doctor controls the emitting switch of radiation after the assistant informs of the completion of positioning or a medical doctor conducts all operations including the positioning of the patient.

Further, for example, in the case of large-scale facilities, it is presumed that a patient has to move around plural floors in the facilities in the time duration from the time of radiographing to the time when a medical doctor starts diagnosis of the patient. However, in the case of small facilities, since the facility is narrow, the moving distance of the patient in the time duration from the time radiographing to the time when the medical doctor starts diagnosis of the patient is short.

Under these conditions, it is hard to imagine that the photographed image mismatches with the patient. Consequently, when the same system as the system used in the large-scale system is used in the small-scale facilities, since it is necessary to generate examination order information starting from the input operation of the patient name, the procedure becomes complicated and the diagnosis efficiency becomes worse.

Further, in order to generate the examination order information including patient information and examination information of the patient in advance and to correlate the examination order information with the photographed image, which has been radiographed, a system, to which respective apparatuses are connected via network corresponding to the main system, such as HIS/RIS, becomes necessary. However, in order to configure this type of system described above, a certain level of cost is necessary, which becomes a problem for a small-scale facility. Further it is not optimum to introduce the same system utilized in the large-scale facilities described above into a small-scale facilities, even though leaving the same configuration concept with decreased number of apparatuses.

Patent Document 1: U.S. Pat. No. 5,334,851
Patent Document 2: Unexamined Japanese Patent Application Publication No. 2002-159476
Patent Document 3: Unexamined Japanese Patent Application Publication No. 2002-311524

SUMMARY

Therefore, an object of the present invention is to provide a diagnosis system, which is capable of simply and surely correlating the photographed image, which has been radiographed, to a patient and preventing the mismatch of the patient and the photographed image without increasing the number of work processes, such as inputting operation of examination order information in advance in the small scale facilities, such as a small medical clinic to solve the problems described above.

To solve the problem, in accordance with an aspect of the present invention, a diagnosis system includes an image generating apparatus for forming image data of a patient obtained by taking a radiograph of the patient and a control apparatus, wherein the image generating apparatus includes a flat panel detector having an image generating device for detecting radiation emitted to the patient, converting the radiation to an electric signal, storing the electric signal and forming the image data based on the electric signal, which has been stored, a storing device, which is capable of storing the image data generated by the image generating device in order of taking a radiograph, and a transmission device, which is capable of transmitting the image data stored in the storing device to the control apparatus in the order of taking the radiograph, and wherein the control apparatus includes a receiving device for receiving the image data transmitted by the transmission device and a correlation device for correlating the image data received by the receiving device with patient information related to the patient corresponding to the image data.

DETAILED DESCRIPTION OF THE PREFERRED EMBODIMENT

In accordance with another aspect of the present invention, in the embodiment described above, the flat panel detector further includes an identification information input device for inputting patient identification information for identifying the subject patient and the storing device stores the photographed image data together with the patient identification information and the transmission device transmits the photographed image data together with the patient identification information to the control apparatus.

In accordance with another aspect of the present invention, in the embodiment described above, the patient identification information is at least either a search ID, which has been given to each patient in advance, or dividing information for dividing subject patients.

In accordance with another aspect of the present invention, in the embodiment described above, the flat panel detector integrally or detachably comprises a display device, which is capable of displaying a patient list of the subject patients, and the identification information input device is to input the patient identification information by selecting a subject patient from the patient list.

An embodiment of a diagnosis system of the present invention will be described by referring to FIGS. 1-7 hereinafter. However, the present invention is not limited to the examples illustrated in the figures.

Figure 1:
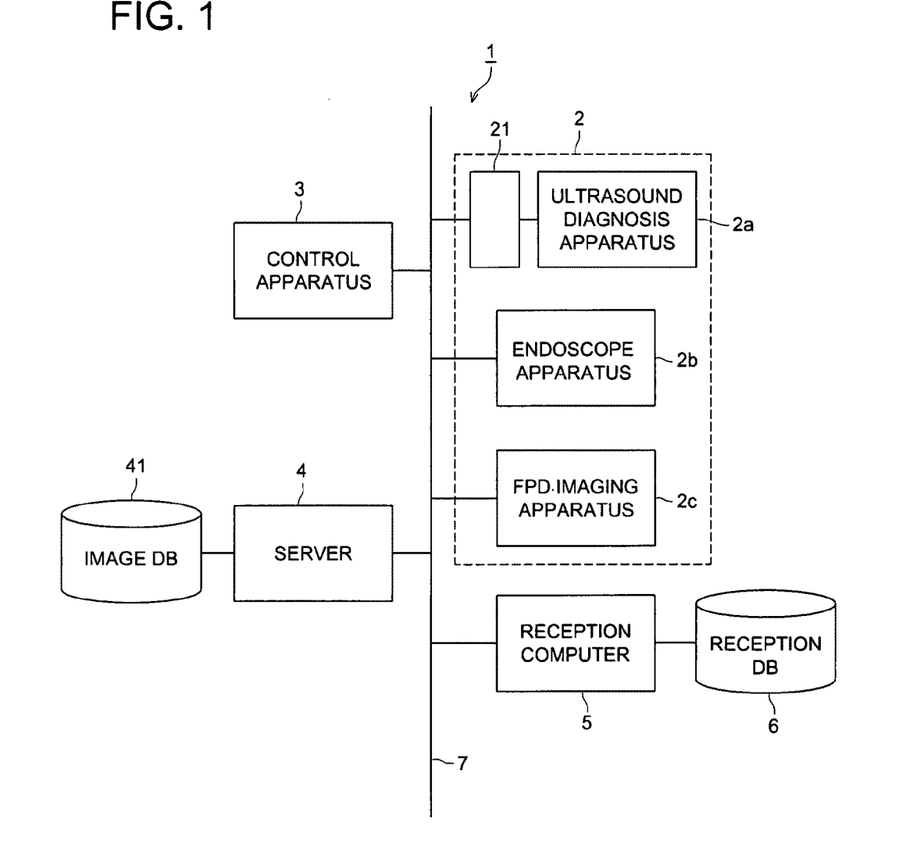
FIG. 1 illustrates a system configuration of an embodiment of a diagnosis system of the present invention.
Figure 2:
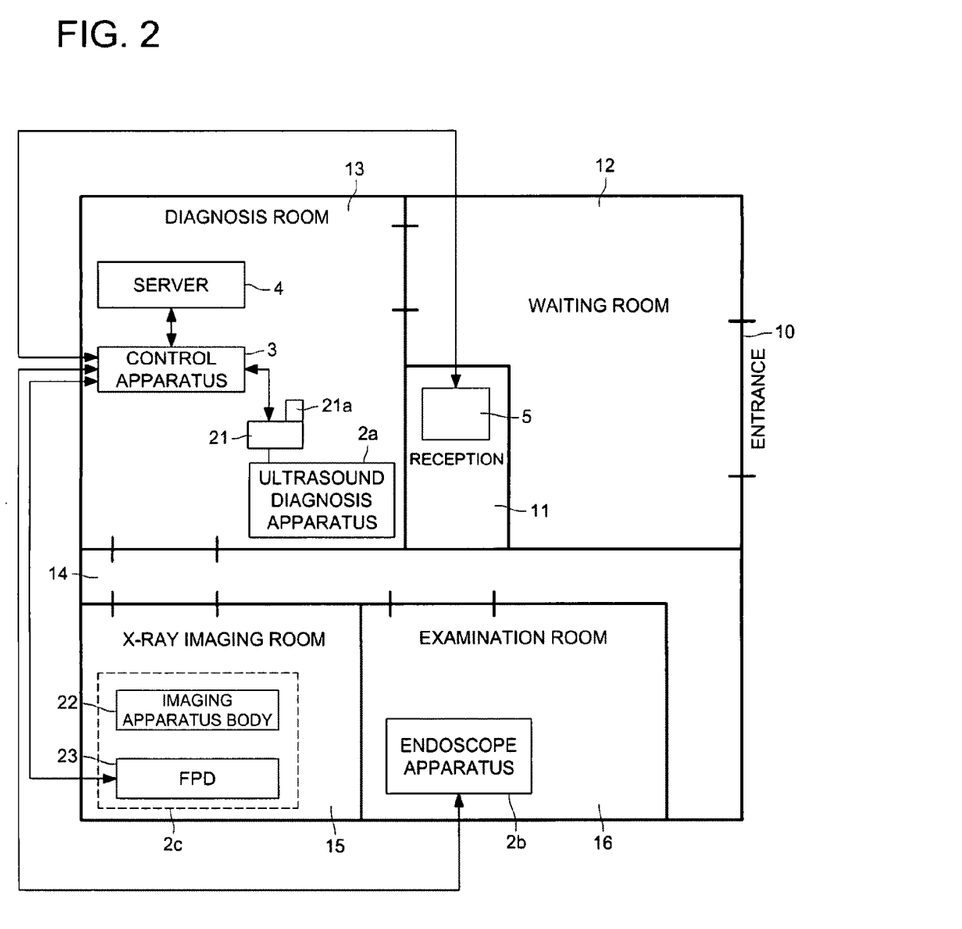
FIG. 2 illustrates an example of the arrangement of respective apparatuses in a medical facility, to which the diagnosis system shown in FIG. 1 is applied.

FIG. 1 illustrates a system configuration of an embodiment of the diagnosis system 1 of the present invention. FIG. 2 illustrates an example of the arrangement of respective apparatuses in a medical facility, to which the diagnosis system shown in FIG. 1 is applied.

A diagnosis system 1 in the embodiment of the present invention is a system applied to a small-scale facility, such as a small medical clinic. As shown in FIG. 1, the diagnosis system 1 comprises an image generating apparatus 2 for generating image data of image data of a photographed image (photographed image data), including an ultrasound diagnosis apparatus 2a, an endoscope apparatus 2b and an FPD imaging apparatus 2c, a control apparatus 3, a server 4 and a reception computer 5. Respective apparatuses are connected to communication network 7 (it will be simply called "network" hereinafter) such as LAN (Local Area Network) via, for example, a switching hub (not shown).

With respect to the communication system in a hospital, in general, DICOM (Digital Image and Communications in Medicine) standard protocol is used. The communication system, which can be applied to the embodiment of the present invention is not limited to these communication systems described above.

For example, in a small-scale facility, such as a small medical clinic, respective apparatuses are arranged as shown in FIG. 2.

Namely, when entering an entrance 10, a reception desk 11 for receiving patients and a waiting room 12 are provided. A receptionist is disposed at the reception desk 11. The receptionist gives a reception number plate, onto which a reception number (order of reception with a serial number of the day) for identifying each patient has been printed, to the patients visited to the clinic. The reception computer 5, which is used for the reception, insurance point calculation and accounting calculation, is provided at the reception desk 11. The receptionist obtains the name of a patient, and inputs the reception number correlated with the name of the patient through the reception computer 5. Further, the receptionist also inputs necessary item for the accounting and the information related to the reception (accounting calculation and insurance point request calculation) (it will be called "reception related information" hereinafter) based on the patient medical record of the patient after completing medical examination of the patient.

Next to the waiting room 12, a diagnosis room 13 where a medical doctor conducts a medical examination and diagnosis, which is isolated by a door and the same, is provided. For example, a controller 3, by which the medical doctor displays the image to conduct image diagnosis, and a server 4 including an image database 41, into which the image data of photographed images is stored, are arranged on the diagnosis desk (not shown) in the diagnosis room 13. Since from the viewpoint of privacy, the necessity of conducting an ultrasound diagnosis in an isolated place is low, an ultrasound diagnosis apparatus 2a is also provided in the diagnosis room 13.

An X-ray imaging room 15 for conducting radiation imaging is provided across a passageway 14, which is facing to the diagnosis room 13. In the X-ray imaging room 15, an FPD imaging apparatus 2c configured by an imaging apparatus 22 and a reading apparatus 23 is disposed. Further, next to the X-ray imaging room 15, an examination room 16 is provided, and an endoscope apparatus 2b is disposed therein.

An diagnosis system 1 in an embodiment of the present invention will be described hereinafter.

Firstly, the configuration of respective apparatuses will be described.

An image generating apparatus 2 is a modality for photographing subject region of a patient to be examined as an object, converting the photographed image into a digital form and forming image data of the photographed image (photographed image data), the image generating apparatus 2 being configured by, for example, an ultrasound diagnosis apparatus 2a, an endoscope apparatus 2b and an FPD imaging apparatus 2c.

The ultrasound diagnosis apparatus 2a is configured by an ultrasound probe for outputting ultrasound and an electronic apparatus for converting the sound waves (echo signals) received by the ultrasound probe into the image data of the photographed image of internal organization (both are not shown). The ultrasound diagnosis apparatus 2a is arranged to transmit ultrasound from the ultrasound probe into the body, to receive the sound waves (echo signals) reflected by the body organization via the ultrasound probe again and to form a photographed image corresponding to the echo signals with the electronic apparatus.

A converting apparatus 21, which is a converting device (a converter) for converting analog signals to digital signals, is connected to the ultrasound diagnosis apparatus 2a. The ultrasound diagnosis apparatus 2a is connected to network 7 via the converting apparatus 21. By interfacing the converting apparatus 21, even when the data, which does not meet the standard (for example, communications protocols) of the external apparatuses connected to the network 7, is outputted from the ultrasound diagnosis apparatus 2a, it becomes possible to transmit and receive data between the ultrasound diagnosis apparatus 2a and the external apparatuses connected to the network 7 by appropriately conducting conversion.

In a conversion apparatus 21, there is provided an input operation section 21a including an input section configured by, for example, a ten-key, a keyboard and a touch panel, and a display section (both are not shown) configured by a monitor such as a CRT (Cathode Ray Tube) or a LCD (Liquid Crystal Display).

The endoscope apparatus 2b is an apparatus in which a small sized imaging device is provided on the edge portion of the pipe having flexibility (not shown). The imaging device is configured by an objective optical system including an optical lens, an imaging section disposed at the focusing point of the objective optical system and a lighting section for conducting lighting necessary for photographing, which is configured by a LED (Light Emitting Diode (not shown) or the like. An imaging section includes a solid state-imaging element, such as CCD (Charge Coupled Device) and CMOS (Complementary Metal-Oxides Semiconductor) to convert the amount of incident lights to electric signals corresponding to the amount of the incident lights when light flux enters into the imaging section. The objective optical system is arranged so as to converge the light flux on the area irradiated by the lighting section and forming an image onto the solid state imaging element provided in the imaging section. The imaging section is arranged to output image data of the photographed image as electric signals by converting the light flux entering into the solid state imaging element.

Figure 3:
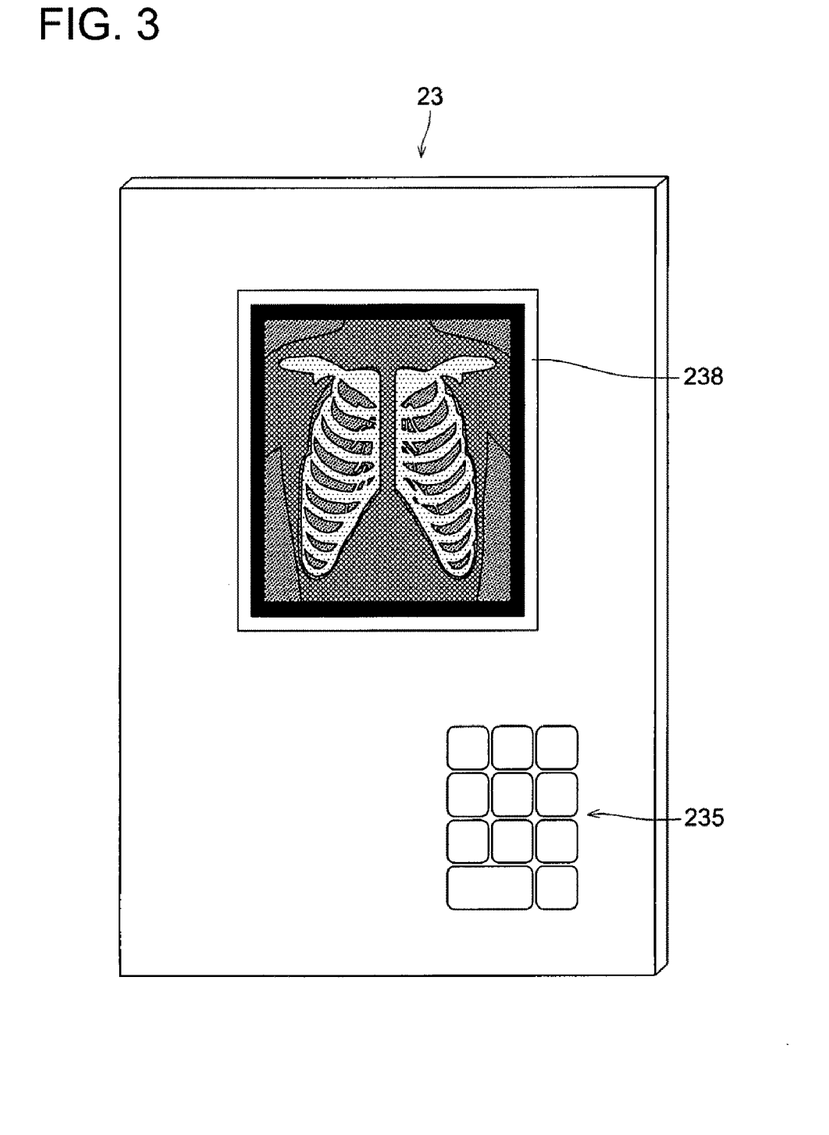
FIG. 3 illustrates a front view showing the schematic configuration of an FPD, which is applied to the diagnosis system shown in FIG. 1.

An FPD imaging apparatus 2c includes an imaging apparatus body 22 having a radiation source for irradiating radiation (not shown) (refer to FIG. 2) and a flat panel detector 23 (it will be called "FPD" hereinafter) shaped in a cassette type, which is portable as shown in FIG. 3.

Figure 4:
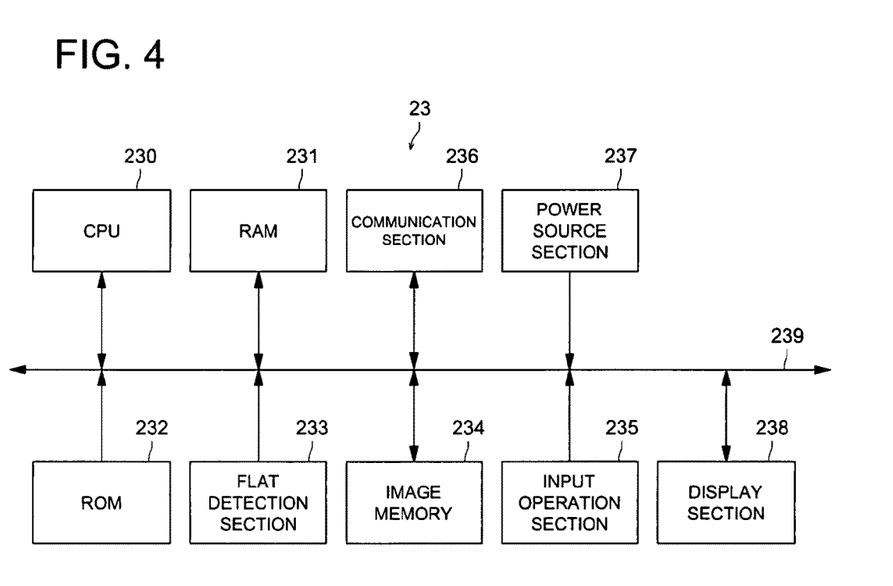
FIG. 4 illustrates a main block diagram showing a schematic configuration of the FPD shown in FIG. 3.

The configuration of the FPD 23 will be described by referring to FIGS. 3 and 4. As shown in FIG. 4, the FPD 23 comprises a CPU 230, a RAM 231, a ROM 232, a flat detection section 233, which is an image generating device for forming photographed image data by detecting radiations, an image memory 234, which is a memory device, an input operation section 235, a communication section 236, a power source section 237 and a display section 238. Respective sections are connected to bus 239.

The flat detection section 233 includes, for example, a glass substrate. A plurality of pixels are arranged at predetermined points on the glass substrate, and the pixels detect the radiation which is irradiated from the radiation source and passes through at least the object, corresponding to the strength of the radiation and convert the detected radiation into electric signals for forming and storing the photographed image data.

Here, with respect to the flat detection section 233, there are some types of detection section. One is, for example, an indirect type having a radiation-light conversion layer for converting radiations to fluorescence (lights) and photoelectric conversion layer for detecting fluorescence converted by the radiation-light conversion layer and converting the fluorescence to electric signals. Another is a direct type having a radiation-electric signal conversion layer including a radiation receiving section for directly converting radiation to electric charges instead of the radiation-light conversion layer and the photoelectric conversion layer. Since the indirect type does not need to use a high voltage source, which is used for the direct type, the indirect type is preferable.

The image memory 234 is configured by, for example, a non-volatile memory, such as, a flash memory. The image memory 234 is arranged to be capable of storing the photographed image data, which has been obtained and formed by the flat detection section 233, according to the photographing order. When patient identification information (which will be described later) for identifying a patient is inputted from the input operation section 235, the image memory 234 stores the photographed image data together with the patient identification information.

The input operation section 235 is configured by, for example, numeral input keys and various function keys. The input operation section 235 functions as an identification information input device for inputting the patient identification information for dividing patients every time when subject patient changes. Here, the input operation section 235 is not limited to the one, which is configured by various keys as shown in FIG. 3. For example, the input operation section 235 may be configured by a touch screen uniformly configured by a display section 238, which will be described later, and a touch panel so that the touch panel covers the display screen of the display section 238.

Here, patient identification information is a search ID such as a reception number issued at the reception desk 11 when the patient visits the clinic. For example, when photographing the patient having a reception number "01", which has been given at the reception desk 11, a technician inputs "01" as a search ID corresponding to the patient through the input operation section 235. In a small medical clinic, in a normal situation, the number of patients visiting the clinic is about 10 (ten)-40 (forty). Thus, two-digit serial number will be enough for the serial number of a patient registration card. Consequently, the input operation section 235 may be configured so that two-digit number can be inputted. The configuration of the input operation section 235 is not limited to the one, which has been described above. For example, an input operation section having an input section such as a card reader for reading information written on a card by inserting the card to the card reader or a bar code reader for reading bar code may be used.

When correlation between the photographed images and the patient is clear without using the search ID used to identify the patient based on the reason that the patients are not many, dividing information which is capable of identifying the number of images taken for the patient when the subject patient changes, (for example, images up to image number A are allocated to the fist patient, and images from image number B are allocated to the second patient), may be inputted. In this case, for example, a button for dividing the patients respectively may be provided in the input operation section 235 so that the image number corresponding to the time a patient changes can be identified by pushing the button for diving the patients just before starting of taking photograph of a new patient. Further, both an input key capable of inputting the search ID and the button for dividing the patients may be provided in the input operation section 235 so that the search ID is inputted for each patient to be photographed, for example, in a normal situation and in an emergency or when patients are not many, an identification signal for identifying the change of the patient can be inputted by using the button for dividing the patients. Namely, both buttons can be used when necessary. In this embodiment, a case of inputting the search ID (reception number) for respective patients as patient identification information will be described below.

A communication section 236 is to conduct receiving and transmitting of data between the FPD 23 and the control apparatus 3, which is an external apparatuses connected to network 7 by a wireless communication system, such as wireless communication LAN or a wired communication system by connecting cables (not shown) to respective apparatuses. The communication section 236 may be configured so that the communication to the control apparatus 3 is conducted by placing the FPD 23 on a cradle, by providing the cradle (not shown) in the X-ray imaging room 15 (refer to FIG. 2). The cradle is connected to the external apparatus, such as the control apparatus 3 via a wireless communication system or a wired communication system and onto which the FPD 23 can be placed.

The communication section 236 is arranged to send photographed image data which have been detected by the flat detection section 233 and stored in the image memory 234, to the control apparatus 3 as a transmission device. Further, when patient identification information for identifying a patient is inputted from the input operation section 235, the communication section 236 transmits the photographed image data to the control apparatus 3 together with the patient identification information.

A power source section 237 includes a rechargeable battery, which supplies power to respective sections configuring the FPD 23. The power source section 237 is configured to be charged via the charge terminal (not shown) provided at the predetermined position of the FPD 23. In this embodiment, the case where the rechargeable battery is provided in the power source section 237 has been described above. However, the power source section 237 may be configured by a primary battery, which can be exchanged. Further, in this embodiment, a case where the power source section 237 is provided inside the FPD 23 has been described. However, the FPD 23 may be configured so as to supply the power via a cable from the outside of the FPD to respective sections configuring the FPD 23.

The display section 238 is configured by a display screen including a CRT (Cathode Ray Tube) or a LCD (Liquid Crystal Display). The display section 238 functions as a display device for displaying a patient list and photographed images on the display screen according to the instruction of the display signal inputted from the CPU 230.

The CPU 230 reads out the predetermined programs stored in a ROM 232, expands the programs in the work area of a RAM 231 and executes various processes according the programs.

Concretely, for example, the CPU 230 controls the switching section of the TFT (Thin Film Transistor) configuring respective pixels of the flat detection section 233, switches the reading operation of the electric signals stored in the respective pixels and obtains the photographed image data, which is detecting results from the flat detection section 233, by reading out the electric signals stored in the flat detection section 233.

Further, the CPU 230 controls the communication section 236 so as to transmit the photographed image data detected and obtained by the flat detection section 233 and the patient identification information inputted from the input operation section 235 to the control section 238. The CPU 230 controls the display section 238 so as to display the patient list, the photographed image data or an image based on reduced image data having less information amount than the photographed image data.

The input operation section 21a of the conversion apparatus 21 in the ultrasound diagnosis apparatus 2a also functions as an identification information input device for adding the search ID as patient identification information to the image data when photographing like the FPD 23 in the FPD imaging apparatus 2c, which is not shown. The identification information input device is also included in the endoscope apparatus 2b or connected to the endoscope apparatus 2b from the outside like the FPD 23 so as to add the patient identification information such as the search ID of the patient to the formed image data of the photographed image.

With respect to the search ID inputted from the identification information input device, as the same as the input operation section 235 described above, for example, the reception number is used. As described above, in the small medical clinic, normally, the number of patients per day is 10-40. Accordingly, two digits are enough for the serial number of the patient registration card. Consequently, with respect to the identification information input device, it is preferable to use a less expensive ten-key, which is capable of inputting this two-digits number.

Further, when the display section is provided together with this identification information input device, this display section may function as the display device for displaying the patient list.

Figure 5:
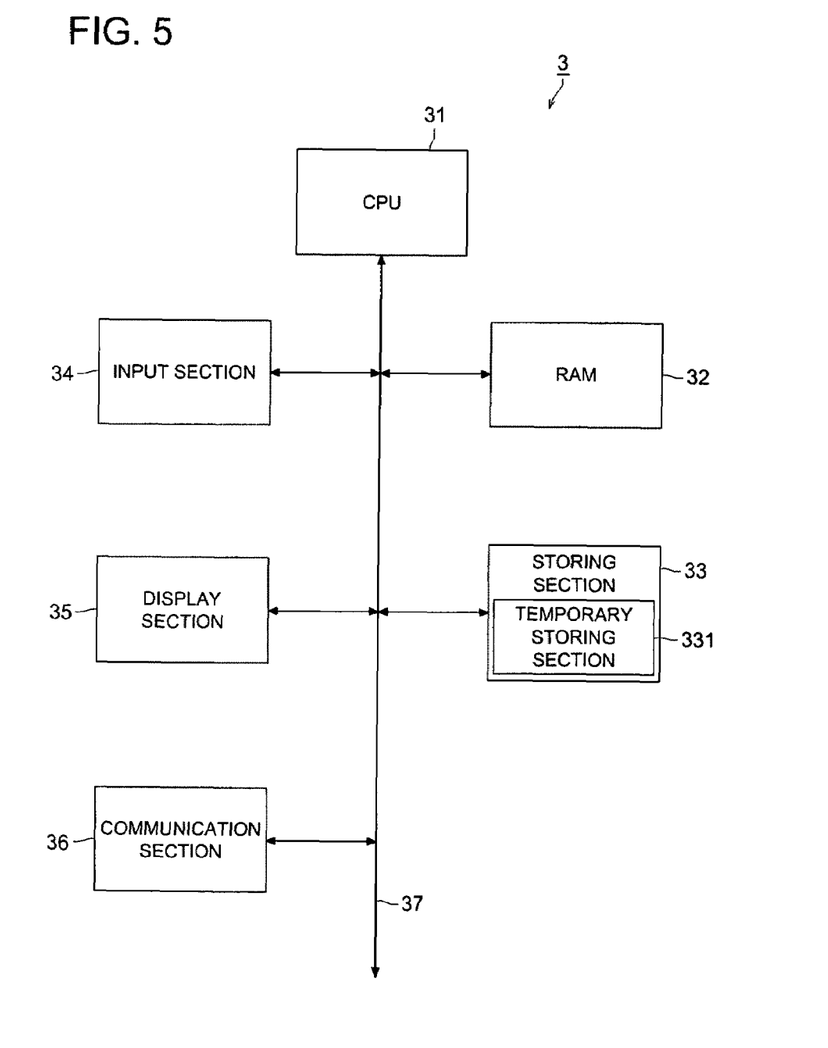
FIG. 5 illustrates a main block diagram showing a schematic configuration of the control apparatus, which is applied to the diagnosis system shown in FIG. 1.

The control apparatus 3 is placed at, for example, a diagnosis room 13 and is a workstation, on which a medical doctor displays images and conducts diagnosis by analyzing the images. The workstation may have a monitor (a display section) having higher definition than the definition of display section of a normal PC (personal computer). As shown in FIG. 5, the control apparatus 3 is configured by a CPU 31, a RAM 32, a memory section 33, an input section 34, a display section 35 and a communication section 36, and respective sections are connected to bus 37.

The CPU 31 is arranged to read out various programs including a system program and process programs stored in the memory section 33 and expand them in the RAM 32. The CPU 31 is arranged to execute image processes, which will be described later, and various processes including the process for correlating the photographed image data, to which image processing operation has been applied, with patient information according to the expanded program.

The memory section 33 is configured by a HDD (Hard Disk) and a semiconductor non-volatile memory. The memory section 33 is storing various programs as described above, region identifying parameters (a lookup table for correlating the outline of the object appeared in the image and the shape with the photographed region) for identifying the photographed region as described in the specifications of Japanese patent application publication No. H11-85950 Open to Public inspections and Japanese patent application publication No. 2001-76141 Open to Public inspections and image process parameters (a lookup table defining the gradation curve used for a gradation process and the emphasis degree of a frequency process) for conducting image processing corresponding to the identified photographed region.

Further, the memory section 33 is arranged to temporally store image data of the photographed image formed by the various image generating apparatuses 2. When the search ID, patient information, information related to the type of photographing and information for identifying the image generating apparatus 2 used for the photographing are added to the photographed image data, the photographed image data are correlated with these information items and stored into the memory section 33. Other than this, the memory section 33 stores various information items, which have been transmitted to the control apparatus 3, such as a patient list, which has been formed in order of reception of the patients.

An input section 34 comprises a keyboard having a cursor, numeral input keys and various function keys, and a pointing device, such as, a mouse (any of them are not shown). The input section 34 is arranged to be capable of inputting a patient name, which is patient information for identifying the subject patient. The input section 34 is also arranged to transmit instruction signals inputted by the key operation to the keyboard and mouse operation to the CPU 31.

Here, with respect to the patient information inputted from input section 34, they can be, for example, a patient name and a patient registration card number. However, the patient information is not limited to these described here. A search ID is to become an identification sign for identifying the examination object when retrieving the photographed image after the photographing and, for example, the reception number given by the reception when checking in may be the identification sign. In this embodiment, an example in which a patient name is inputted as patient information and a reception number is inputted as a search ID will be described.

A display section 35 is configured by a monitor including, for example, a CRT (Cathode Ray Tube) or a LCD (Liquid Crystal Display). As described later, the display section 35 is a display device for displaying photographed images based on the photographed image and various patient information items. The display section 35 displays various screens according to the instructions of the display signals inputted from the CPU 31.

Figure 6:
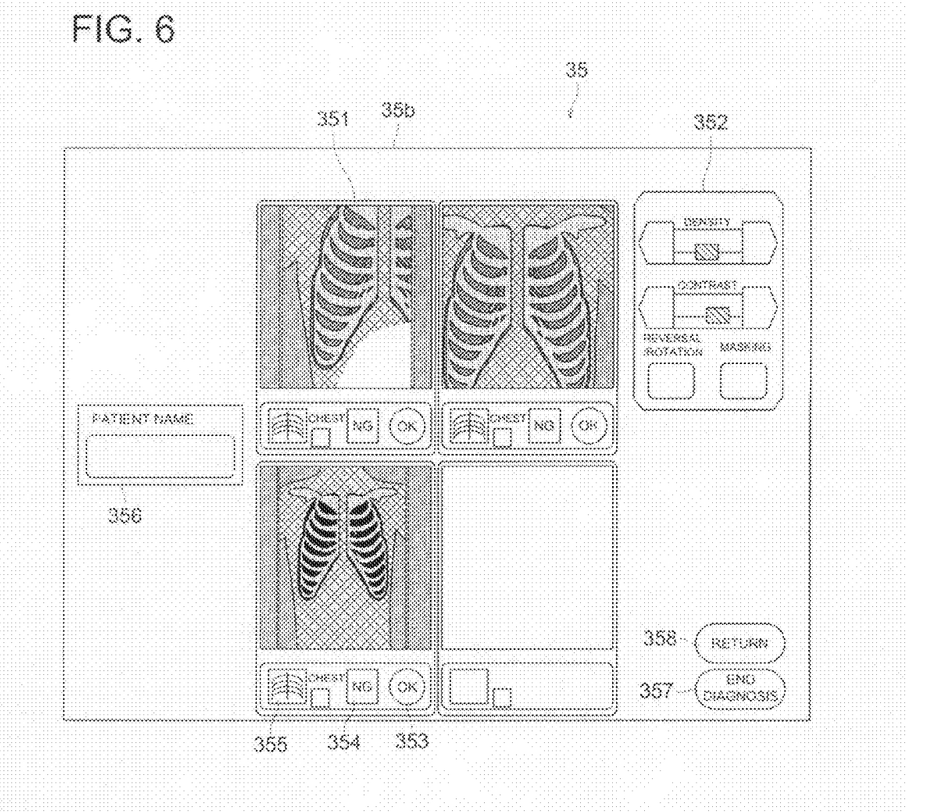
FIG. 6 illustrates an example showing an image confirmation screen of the diagnosis system shown in FIG. 1.

In this embodiment, for example, when a medical doctor inputs the instruction signal through the input section 34 for displaying the photographed images, which have been obtained from an image generating apparatus such as the ultrasound diagnosis apparatus 2a, the endoscope apparatus 2b and the FPD imaging apparatus 2c, an image confirmation screen 35b is displayed on the display section 35, as shown in FIG. 6.

As shown in FIG. 6, the image confirmation screen 35b includes an image display field 351 for displaying a photographed image based on the photographed image data formed by the various image generating apparatuses 2 and an image process condition adjustment field 352 for inputting the adjustment instruction of the image process conditions. Further, arranged in the image display field 351, corresponding to each display field of the image display field 351, are an OK button 353 for determining the photographed image displayed in each display field and storing the image data of the photographed image, which has been determined, a NG button for instructing the deletion of the image data of photographed image displayed on each display field and re-outputting of image data and a photographed region display field 355 for displaying the photographed region, which is determined based on the automatic region recognition for recognizing which region of the patient has been photographed for respective photographed images. When storing the determined image data of the photographed image, a mark showing that the related image has been stored may be displayed in each display field of the image display field 351.

Further, on the image confirmation screen 35b, a patient name field 356 for inputting and displaying the patient name as patient information is provided. In this embodiment, the example, in which the patient name field 356 is provided as an input and display field of the patient information, will be described hereinafter. However, the input and display field of the patient information is not limited to the one described here as an example.

Other than this, in the image confirmation screen 35b, a diagnosis end button 357 for completing the diagnosis and a return button 358 for returning to the previous display screen are provided. Here, the configuration of the image confirmation screen 35b is not limited to the example shown in FIG. 6. For example, a display field for displaying other than these described above or a button other than these described above may be provided. For example, the display field for displaying a reception number corresponding to the patient list may be provided.

A communication section 36 is configured by network interface. The communication section 36 is arranged to conduct data communication via a switching hub with external apparatuses connected to the network 7. Namely, the communication section 36 is a receiving device for receiving image data of the photographed image formed by the image generating apparatus 2 and is also an output device for outputting image data of the photographed images, the image process of which has been completed and confirmed, to the external apparatus, such as a sever 4 when necessary.

Next, the various processes performed by the CPU 31 will be described.

In this embodiment, the CPU 31 functions as an image extraction device for extracting only image data of photographed image taken for a specific patient among the photographed image data stored in the memory section 33 based on the patient identification information of the search ID or the dividing information for dividing patients.

Namely, as described above, in the case where the search ID, which has been correlated with the patient information of the subject patient, has been inputted from the input operation section 21a or the input operation section 235 of the FPD23 when photographing, this search ID is added to the image data of the photographed image as header information. When an operator, such as, a medical doctor inputs instruction signals for extracting the photographed image corresponding to the search ID from an input section 34, the CPU 31 retrieves the photographed image having the search ID, extracts and displays the photographed image onto the image confirmation screen 35b of the display section 35.

When the dividing information for showing the time at which the subject patient changes to a next patient is simply inputted from the input operation section 235 of the FPD 23, the CPU 31 correlates, for example, image number A to image number B to the first patient and correlates a image number C to image number D to the second patient among the photographed images stored in the memory section 33 by referring to the patient list. Then, when an operator, such as a medical doctor selects a certain patient from the patient list, the CPU 31 extracts only photographed images of the patient and displays them onto the image confirmation screen 35b on the display section 35.

Further, the CPU 31 performs the image processing of the image data of the photographed images, which have been formed by the image generating apparatus 2 and received by the communication section 36, corresponding to the photographed region of the body and functions as an image processing device for forming photographed image suitable for the diagnosis.

Concretely, the CPU 31 firstly reads out region identification parameters from the memory section 33, and performs an automatic region identification process for identifying the photographed region based the outline and the shape of the photographed object appearing on the photographed image formed by the image generating apparatus 2. Once the region of the photographed image is identified, the CPU 31 reads out the image process parameters corresponding to the photographed region from the memory section 33, determines the image process conditions based on the read parameters and applies the image processing to the image data, such as a gradation process for adjusting contrast of the image, a process for adjusting density and a frequency process for adjusting sharpness based on the determined image process conditions. Further, when an operator, such as a medical doctor inputs the adjustment of the density and the contrast of the photographed images from an image process condition adjustment field 352, the CPU 31 performs the image processing of the photographed images corresponding to this operation. Then, when completing the image processes and having pushing down the OK button 353, the CPU 31 determines the image data of the photographed images, to which image processing have been applied, as the diagnosis image data of the photographed image.

Further, when the patient information for identifying the photographed examination object has been inputted, the CPU 31 replaces the patient information, such as this patient name, with the search ID, conducts the process for correlating the patient information to the photographed image data, to which a certain image process has been applied, and functions as a device for correlating the photographed image data to the patient information and storing them. The CPU 31 writes and stores the photographed image data correlated to the patient information into the memory section 33 or an image database DB 41 of the server 4.

Further, the CPU 31 may be arranged to transmit the instruction signal to a reception computer 5 so as to send information of a predetermined patient among the reception related information stored in reception DB 6, as described later. When the reception computer 5 has transmitted the reception related information, the CPU 31 correlates the reception related information to the photographed image data, to which the same patient information as the reception related information has been correlated. When the patient information, the reception related information and the photographed image data are correlated each other, the CPU 31 writes and stores the patient information, reception related information and the photographed image data, which have been correlated each other into the image database DB 41.

In FIG. 1, a server 4 is a computer configured by a memory section including a CPU, a RAM and a HDD, and a communication section (any of them is not shown) for controlling communications with various apparatuses connected to network 7. The server 4 including image database DB 41, correlates the image data of photographed images, to which the control apparatus 3 gives the writing instruction via communication section, with the supplemented information (information including patient information) and stores them to the image database DB41 as an image storing device by executing software process under the collaboration of programs stored in CPU and memory section. Further the server 4 retrieves the image data and its supplemented information in the image database DB41 in response to the request from the control apparatus 3, reads the image data and its supplemented information corresponding to the request and transmits them to the control apparatus 3.

Further, the reception computer 5 is a computer apparatus for conducting the reception and registration of the patient visited to the clinic, accounting calculations and insurance point calculation. The reception computer 5 is a computer including a CPU, a RAM, a memory section, an input section, a display section, a communication section (any of them is now shown) and reception DB 6. The respective sections are connected each other via bus.

The CPU reads out various programs such as a system program or process programs stored in the memory section, expands them in the RAM, executes various processes according to the expanded programs and functions as, for example, a reception registration device, a list generating device and a reception information generating device.

The memory section comprises a HDD (a Hard Disk) and a semiconductor non-volatile memory and stores the system program and various process programs executed by the CPU and various data.

The input section is configured by a keyboard including a cursor key, numeral input keys and various function keys, and a pointing device such as a mouse. The input section outputs the push-down signals of key by the push-down operation of the keyboard and operation signals of the mouse to the CPU as an input signals.

The display section includes a monitor, for example, a CRT or a LCD and displays various screens according to the instruction of the display signals inputted from the CPU.

A communication section is configured by network interface. The communication section conducts data communication between the external apparatuses connected to the network.

Figure 7:
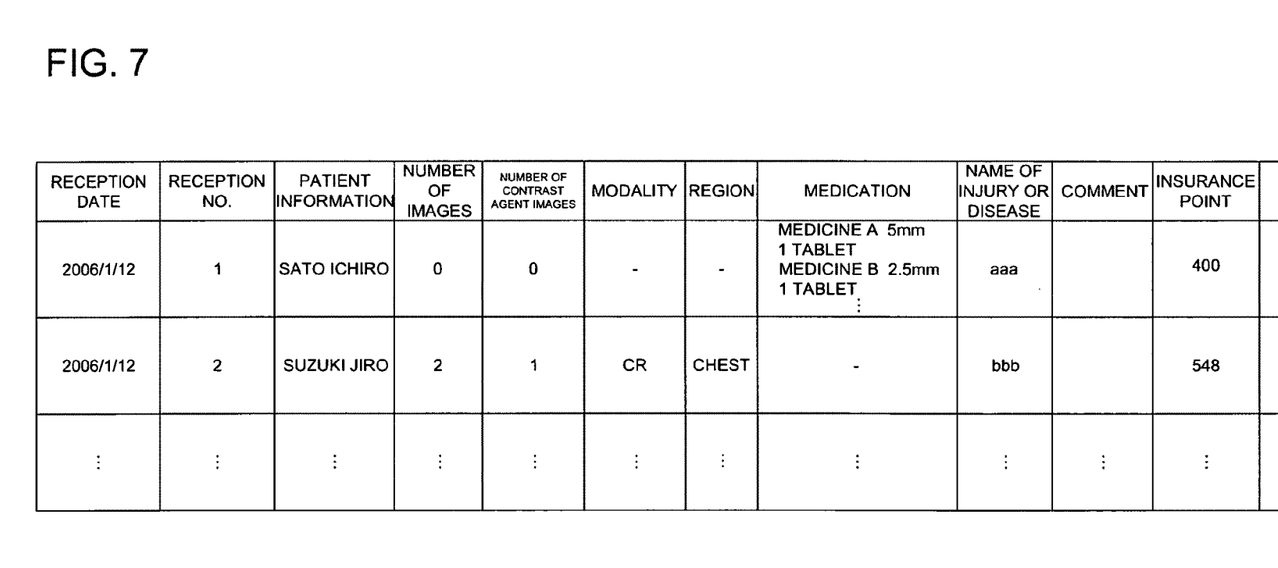
FIG. 7 illustrates an example of data storage of reception DB shown in FIG. 1.

A reception DB 6 is a database for storing the reception related information related to the patient who visited to the clinic, which has been correlated with the patient information. An example of data storage of the reception DB 6 is illustrated in FIG. 7. The reception DB 6 is a database, in which the reception related information of respective patients who visited the clinic is stored. As shown in FIG. 7, the reception DB 6 includes a "reception date" row for storing the reception date of a patient, a "reception No." row for storing the reception No., which has been given to the patient, a "patient information" row for storing the patient information (here, it is a patient name), a "number of images" row for storing the number of images of the patient photographed on the reception date, a "number of contrast agent images" row for storing the number of images in which the contrast agent has been used, a "modality" row for storing the type of the image generating apparatus 2 used for the photographing, a "region" row for storing the photographed region, a "medication" row for storing the information of medicine prescribed for the patient on the reception date, a "name of injury or disease" row for storing the name of injury or decease, which the medical doctor diagnosed on the reception date, a "comment" row for storing the comment inputted from a control apparatus 3, which will be described later and an "insurance point" row for storing calculated insurance points.

Next, the operation of a diagnosis system 1 of an embodiment of the present invention will be described.

Firstly, a reception number is given to the patient who visited the clinic at a reception desk 11 and the reception number plate is issued. A receptionist conducts hearing of the patient name and inputs the reception number, which is a search ID, and the patient name, which is patient information, from the input section via a reception input screen of the reception computer 5 (not shown). When completing the input operation of the reception number and the patient name, a new record is added to the reception DB 6 and the reception number and the patient name are written thereto.

When the patient, to whom the reception number has been given, moves to an examination room 13, a medical doctor conducts medical examination by interview of the patient and determines the photographing and examination to be conducted. When having determined that the photographing of the patient is necessary for the medical examination by interview, a conductor of the photographing, who conducts the photography, such as a medical doctor or a assistant, takes the patient to the place where the image generating apparatus 2 used for the photogrphing is set and inputs the reception number (a search ID) given to the patient from the input operation section of the image generating apparatus 2. For example, when an ultrasound diagnosis apparatus 2a is used as the image generating apparatus 2, the conductor of the photography inputs the reception number of the patient as the search ID from the input operation section 21a, or input operation section 235 of the FPD 23 when the FPD imaging apparatus 2c is used as the image generating apparatus 2, so that the image generating operation of the image generating apparatus 2 becomes ready to start operation.

After that, the conductor for the imaging conducts photographing (imaging) of the examination object region of the patient as a subject, and the image generating apparatus 2 forms image data of the photographed image. When the examination reservation has been made in advance on the date, the patient may directly move from the reception desk to the imaging room 15 or the examination room 16 without receiving the medical examination by interview. For example, when the photographing has been conducted and the photographed image data has been formed by the FPD imaging apparatus 2c, the image data of the photographed image is stored in the image memory 234 of the FPD 23 in order of photographing. Further, the display section 238 of the FPD 23 displays a reduced image having a smaller information amount than the photographed image or the photographed image data so that the conductor of photographing (a technician or a medical doctor) can determine whether or not the photographing is appropriate, especially whether or not the positioning of the patient is appropriate by checking the display on the display section 238.

After selecting a patient, another patient may be selected. In this case, the selected patient may be photographed in the order or simultaneously (or in parallel) by respective image generating apparatuses 2. Even in this case, since the search ID as patient identification information per a patient is inputted when photographing is conducted by the image generating apparatus 2, it is possible to correlate the patient to the image data after the photographing by checking the search ID added to the image data.

When conducting photographing by using only the FPD imaging apparatus 2c, the image data of the photographed image may be stored in the image memory 234 in order of photographing, together with dividing information of the patient by inputting only the dividing information of the patients for indicating the end of a patient from the input operation section 235. When the patient list can be displayed onto the display section 238, the patient identification information for identifying the subject patient may be inputted by selecting the subject patient in the patient list, and the selected patient may be correlated with the photographed image data and stored into the image memory 234.

When the photographing has been completed and the instruction so as to transmit the photographed image data to the control apparatus 3 has been inputted from the input operation section 21a or the input operation section 235 of the FPD 23, the formed photographed image data is sent to the control apparatus 3 through the network 7, with the inputted patient identification information such as search ID added thereto. When photographing a patient, who has not stopped by the reception desk in an emergency situation or the like, it becomes possible to extract the image data after photographing with clear distinction of other image data as the same as the normal flow by setting a predetermined code showing an emergency interruption, for example, "99", which does not appear in a normal photographing, as a patient identification information.

When conducting photographing by using the FPD imaging apparatus 2c, the system may be arranged to automatically start transmission of the photographed image data to the control apparatus 3 as soon as the FPD 23 is placed on the cradle. The transmission of the photographed image data stored in the image memory 234 of the FPD 23 to the control apparatus 3 may be conducted per each search ID of a patient or each group of image data divided by the dividing information or by transmitting all the photographed image data stored in the image memory 234 at once.

When the image data of the photographed image is sent from the image generating apparatus 2 to the control apparatus 3, the CPU 31 automatically identify the photographed region. When the photographed region is identified, the CPU 31 determines the image process condition corresponding to the photographed region and conducts the image process of the image data of the photographed image corresponding to the condition. When conducting the image process, the photographed image is stored into the memory section 33 once together with various information items associated with the image data.

When a medical doctor conduct diagnosis of a patient after photographing or an examination, the medical doctor displays the image search screen (not shown) on the display section 35 by operating the input section 34 of control apparatus 3, and inputs the reception number of the patient after having confirmed the reception number of the patient (search ID) from the input section 34. When inputting the reception number, which is a search ID, the CPU 31 extracts the images corresponding to the patient from storing section 33 by using the reception number as a search key, and the extracted photographed images are listed on the image confirmation screen 35b (refer to FIG. 6) of display section 35. The medical doctor obtains the patient name, which is patient information, by interview and inputs it from a patient information input field 356. When inputting the patient information related to the patient from the input section 34 via the patient information input field 356, the patient information inputted as complementary information of the image data of the displayed photographed image is written.

When the photographing has been conducted by using the FPD imaging apparatus 2c and the photographed image data is transmitted to the control apparatus 3 together with the dividing information for diving the patients, the CPU 31 correlates the photographed image data with a corresponding patient by comparing the photographed image data transmitted from the FPD 23 in order of photographing with the patient list stored in the memory section 3. When the patient information is inputted from the input section 34, the CPU 31 extracts the image data corresponding to the patient and displays them onto the image confirmation screen 35b in the display section 35.

The medical doctor checks the image data of the photographed image by the image confirmation screen 35b. When there is no problem with the image data, the medical doctor fixes the photographed image as a photographed image for examination by using OK button 353. On the other hand, there is a problem with the image process of the photographed image, the operator, such as a medical doctor adjusts the density and contrast of the photographed image by using image process condition adjustment field 352. When the image process corresponding to the photographed region has not been appropriately conducted, the parameter correction may be conducted by reflecting the density and contrast adjustment of the photographed image conducted via the image process condition adjustment field 352 to the image process parameters. When the photographed images displayed on respective display fields are indistinct and the density and contrast adjustments cannot adjust the indistinctness, the medical doctor operates the NG button 354 to instruct the deletion of the image data of the photographed image and the re-output of the image data of the photographed image from the image generating apparatus 2.

The medical doctor conducts examination while watching the photographed image which has been photographed on the day after the determination of the photographed image. The medical doctor writes down his or her diagnosis of the patient (name of injury or disease), the medication information indicating the prescribed medicine for the patient, the information related to the photographing and examination conducted to the patient (the type of apparatus used for the photographing, the number of images, yes or no of the usage of contrast agent images, the photographed region, the direction of photographing, the kind of examination, the examination ID) on the medical record sheet. The medical doctor writes the diagnosis on the medical record sheet, at the same time, correlates the image data of the photographed image, which has been photographed on the day, to the patient information, which has been inputted, (deeming the patient information as supplementary information of the patient) and stores them to the memory device, such as image DB 41 of the server 4.

The medical doctor gives the medical record sheet to the receptionist of the reception desk 11 after writing the diagnosis on the medical record sheet. The receptionist gets the examination information input screen displayed on the display section of the reception computer 5, and inputs the reception related information for the insurance point request process based on the medical record sheet from the input section via the examination information input screen. The CPU of the reception computer 5 works out the accounting related information relating to the insurance point calculations based on the number of images of the photographs for the patient, the kind of photograph such as simple radiographing by radiation or contrast agent image radiographing, the type of the image generating apparatus 2 used for the photographing and information added to the image data of the photographed images. The reception related information, which has been inputted, and the insurance points, which have been calculated are correlated with the patient name, which is patient information, and written and stored into the reception DB 6.

As described above, in accordance with the diagnosis system 1 of an embodiment of the invention, when photographing the subject patient by using an image generating apparatus 2, such as an FPD imaging apparatus 2c, patient identification information for identifying the patient, such as, search ID for specifying a patient or dividing information for dividing patients will be inputted and the image data of photographed image will be stored in the image memory 234 of the FPD 23 together with the patient identification information in order of photographing. Thus, when transmitting the image data of the photographed image from the image generating apparatus 2 to the control apparatus 3, the photographed image can be correlated with the subject patient, and the occurrence of the mismatch between the photographed image and the patient can be prevented without conducting issuance of the examination order information (an input operation) in advance, and therefore, the diagnosis efficiency can be improved.

Since it is possible to simply input the patient identification information by inputting either the search ID or the dividing information or by selecting the subject patient from the patient list displayed on the display device, it becomes possible to prevent the mismatch between the photographed image and the subject patient by correlating the photographed image with the patient simply and surely, and improve the diagnosis efficiency without increasing complicated work process, such as inputting the examination order information in advance.

Figure 8:
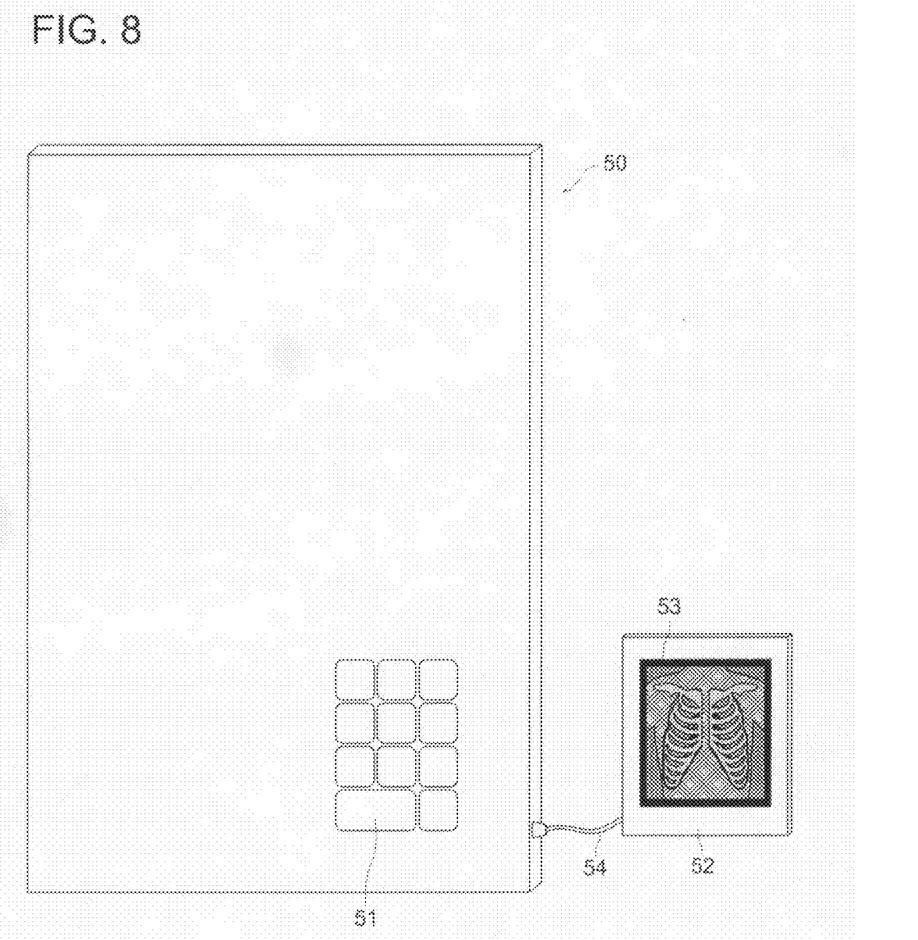
FIG. 8 illustrates a front view of a modification example of the FPD shown in FIG. 3.

Meanwhile, in the embodiment of the invention, as shown in FIG. 3, the FPD 23 is arranged to have the input operation section 235 and the display section 238 in its configuration, the configuration of the FPD 23 is not limited to this configuration. For example, as shown in FIG. 8, only input operation section 51 is provided to the FPD 50 and the display apparatus 52 having the display section 53 may be separately provided. In this case, the photographed image data stored in the image memory 234 of the FPD 50 can be displayed on the display section 53 of the display apparatus 52, for example, by providing a connector for connecting the cable of external apparatus on the side surface of the FPD 50 and connecting the cable 54 of the display apparatus 52 with the connector.

Further, in the embodiment of the invention, there has been described an example, which includes an ultrasound diagnosis apparatus 2a, an endoscope apparatus 2b and an FPD imaging apparatus 2c as an image generating apparatuses 2. However, the image generating apparatus 2 needs to have only functions for photographing the subject patient and forming photographed images based on the imaged data obtained by the photographing, and is not limited to the example described above. It is possible to apply an arbitrary apparatus for forming photographed images, such as, an image generating apparatus using other radiographic image conversion medium, an image generating apparatus for obtaining image data without using radiographic image conversion media, and forming photographed images based on the image data and an image generating apparatus for taking out radiographic images as digital signals by using a radiation detector. Concretely, for example, a CT (Computed Tomography), a MRI (Magnetic Resonance Imaging), a CR (Computed Radiography) apparatus and a mamography may be used other than the ultrasound diagnosis apparatus 2a, the endoscope 2b and the FPD imaging apparatus 2c, which have been described in the embodiment of the invention.

Further, in the embodiment of the invention, the photographed image data which have been determined and the patient information correlated thereto are to be stored in the server 4. However, the storing method for storing the photographed image data and the patient information correlated thereto is not limited to this. For example, a system may be configured so that the memory section 33 of the control apparatus 3 can be used as a memory device for storing the photographed image data and the patient information correlated thereto.

Further, in the embodiment of the invention, the search ID is arranged to be inputted per each photographing operation. However, as the same as the case of inputting the dividing information for dividing patients, when a plurality of photographing operations is conducted for the same patient, the search ID is inputted every time, at which the patient changes and the search ID input operation may be omitted for the second photographing operation. Even in this case, when the FPD 23 is used, since the photographed image data obtained by the photographing is stored into the image memory 234 of the FPD 23 in order of photographing, it is possible to correlate respective images to the search IDs and finally correlate the images divided by a search ID with the patient information as the information belonging to the same patient by the same process when the dividing information of patients is inputted.

It is apparent that the present invention is not limited to the above embodiment and various changes and modification may be made.

In accordance with an embodiment of the present invention, an image generating apparatus for radiographing a patient and forming photographed image data of the patient, includes a flat panel detector, which includes a storing device capable of storing the photographed image data in order of photographing and a transmission device capable of transmitting the photographed image data stored in the storing device to a control apparatus in order of photographing, and the control apparatus is arranged to correlate the photographed image data transmitted from the image generating apparatus with the patient information related to the patient corresponding to the photographed image data. According to this configuration, it becomes possible to simply and surely correlate the photographed image with the patient and prevent the mismatch between the photographed image and the patient without increasing a complicated work process for issuing an examination order (input operation of the examination order information) in advance, and the diagnosis efficiency can be improved.

In accordance with an embodiment of the present invention, the storing device of the flat panel detector is to store the photographed image data together with the patient identification information for identifying a patient, and the photographed image data is transmitted to the control apparatus together with the patient identification information. Thus, even when photographing a plurality of patients by one flat panel detector, it is easy to identify which photographed image data corresponds to which patient. When CR cassettes are used, if the cassettes are inserted in a reading apparatus in the wrong order after photographing, mis-correlation between the patients and the images occurs. However, in the case of FPD, such kinds of problems do not happen. Accordingly, it becomes possible to simply and surely correlate the photographed images with the patient, and prevent the mismatch between the photographed images and the patient without increasing the complicated work process, such as inputting examination order information in advance. As a result, the effect by which the diagnosis efficiency is improved can be achieved.

In accordance with an embodiment of the present invention, since in the flat panel detector, a system is arranged to identify a patient by inputting either a search ID or dividing information, it becomes possible to simply and surely correlate photographed images and a patient, to prevent the mismatch between the photographed image and the patient and to obtain the effect by which diagnosis efficiency can be improved, without increasing a work process, such as inputting examination order information in advance.

In accordance with an embodiment of the present invention, since it is possible to simply input patient identification information by selecting a subject patient from the patient list displayed on the display device, it becomes possible to simply and surely correlate a photographed image and the patient, to prevent the mismatch between the photographed image and the patient and to obtain the effect by which diagnoiss efficiency can be improved without increasing a complicated work process.

What is claimed is:

1. A diagnosis system in which a patient is photographed without radiographing order information to generate image data, and after the photographing, the image data are correlated with patient information, the diagnosis system comprising, an image generating apparatus for generating radiographed image data of a patient by radiographing the patient; and a control apparatus, wherein the image generating apparatus includes a portable flat panel detector, which comprises:

an image generating device for detecting radiation emitted to the patient, for converting the radiation to an electric signal, for storing the electric signal, and for generating the radiographed image data based on the stored electric signal;

a storing device, which is adapted to store a plurality of sets of the radiographed image data, corresponding to a plurality of images, generated by the image generating device, in order of radiographing; and a transmission device, which is adapted to transmit the radiographed image data stored in the storing device to the control apparatus; and wherein the control apparatus comprises:

a receiving device for receiving the radiographed image data transmitted by the transmission device; and a correlation device for correlating the radiographed image data received by the receiving device with patient information related to a patient corresponding to the radiographed image data.

2. The diagnosis system of claim 1, wherein the flat panel detector further comprises:

an identification information input device for inputting patient identification information for identifying a patient who is a radiographing subject, wherein the storing device stores the radiographed image data together with the patient identification information and the transmission device transmits the radiographed image data together with the patient identification information to the control apparatus.

3. The diagnosis system of claim 2, wherein the patient identification information comprises at least one of a search ID which has been given to each patient in advance and dividing information for dividing patients who are radiographing subjects.

4. The diagnosis system of claim 2, wherein the flat panel detector integrally or detachably comprises a display device, which is adapted to display a patient list of patients that are radiographing subjects, and the identification information input device inputs the patient identification information by selecting a patient who is a radiographing subject from the patient list.

* * * * *